(12) United States Patent
Jung et al.

(10) Patent No.: US 10,368,773 B2
(45) Date of Patent: Aug. 6, 2019

(54) APPARATUS FOR MEASURING BODY FAT AND METHOD THEREOF

(71) Applicant: SAMSUNG ELECTRONICS CO., LTD., Suwon-si (KR)

(72) Inventors: Myounghoon Jung, Bucheon-si (KR); Kak Namkoong, Seoul (KR); Kunsun Eom, Seoul (KR); Yeolho Lee, Anyang-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 869 days.

(21) Appl. No.: 14/791,593

(22) Filed: Jul. 6, 2015

(65) Prior Publication Data

US 2016/0106337 A1 Apr. 21, 2016

(30) Foreign Application Priority Data

Oct. 21, 2014 (KR) .................. 10-2014-0142773

(51) Int. Cl.
*A61B 5/00* (2006.01)
*A61B 5/053* (2006.01)

(52) U.S. Cl.
CPC .......... *A61B 5/0537* (2013.01); *A61B 5/4872* (2013.01); *A61B 5/681* (2013.01); *A61B 5/7278* (2013.01); *A61B 2560/0468* (2013.01)

(58) Field of Classification Search
CPC ..... A61B 5/0537; A61B 5/4872; A61B 5/681; A61B 5/7278; A61B 2560/0468
See application file for complete search history.

(56) References Cited

U.S. PATENT DOCUMENTS

| | | | |
|---|---|---|---|
| 6,370,425 B1 | 4/2002 | Oguma | |
| 6,509,748 B1* | 1/2003 | Cheng | A61B 5/0537 324/692 |
| 6,567,692 B1* | 5/2003 | Kohashi | A61B 5/0537 600/547 |
| 8,831,898 B2 | 9/2014 | Pinter et al. | |
| 9,259,169 B2 | 2/2016 | Hamaguchi et al. | |
| 2005/0215919 A1* | 9/2005 | Kim | A61B 5/0245 600/554 |
| 2006/0224080 A1 | 10/2006 | Oku et al. | |

(Continued)

FOREIGN PATENT DOCUMENTS

| | | |
|---|---|---|
| CN | 200966617 Y | 10/2007 |
| CN | 101641046 A | 2/2010 |

(Continued)

OTHER PUBLICATIONS

Communication dated Feb. 16, 2016 by the European Patent Office in counterpart European Application No. 15190836.5.
Communication dated Sep. 12, 2017, issued by the European Patent Office in counterpart European Application No. 15190836.5.

(Continued)

*Primary Examiner* — Rene T Towa
(74) *Attorney, Agent, or Firm* — Sughrue Mion, PLLC

(57) ABSTRACT

Provided is a method of measuring body fat of a user, the method including: measuring a first impedance by using a 4-point measuring method; measuring a second impedance by using a 2-point measuring method; determining a bio impedance by using the first impedance and the second impedance; and determining a body fat percentage by using the bio impedance and body information of the user.

19 Claims, 13 Drawing Sheets

(56) References Cited

U.S. PATENT DOCUMENTS

| | | | | |
|---|---|---|---|---|
| 2008/0001735 A1* | 1/2008 | Tran | ................... | G06F 19/3418 340/539.22 |
| 2009/0047645 A1* | 2/2009 | Dibenedetto | .......... | G16H 15/00 434/258 |
| 2010/0100003 A1* | 4/2010 | Chetham | .............. | A61B 5/0537 600/547 |
| 2011/0208458 A1* | 8/2011 | Pinter | .................... | A61B 5/053 702/65 |
| 2012/0172747 A1 | 7/2012 | Fukuda et al. | | |
| 2014/0296662 A1* | 10/2014 | Hayn | ................... | A61B 5/4875 600/306 |

FOREIGN PATENT DOCUMENTS

| | | | | |
|---|---|---|---|---|
| CN | 102186414 A | 9/2011 | | |
| DE | 202 00 048 U1 | 5/2002 | | |
| GB | 2390429 A | * | 1/2004 | ........... A61B 5/0537 |
| JP | 11-299752 A | 11/1999 | | |
| JP | 2001-145607 A | 5/2001 | | |
| JP | 4723990 B2 | 7/2011 | | |
| JP | 2012-50777 A | 3/2012 | | |
| JP | 2014-110853 A | 6/2014 | | |
| KR | 10-2007-0044825 A | 4/2007 | | |
| KR | 10-0885396 B1 | 2/2009 | | |

OTHER PUBLICATIONS

Communication dated Dec. 27, 2018, issued by the State Intellectual Property Office of P.R. China in counterpart Chinese Application No. 201510382986.8.

* cited by examiner

APPARATUS FOR MEASURING BODY FAT AND METHOD THEREOF

RELATED APPLICATION

This application claims priority from Korean Patent Application No. 10-2014-0142773, filed on Oct. 21, 2014, in the Korean Intellectual Property Office, the disclosure of which is incorporated herein by reference in its entirety.

BACKGROUND

1. Field

Methods and apparatuses consistent with exemplary embodiments relate to a method and an apparatus for measuring body fat.

2. Description of Related Art

Traditionally a bio impedance is measured by using large electrodes placed in contact with the body of a user and the body fat is determined from the measured bio impedance. Accordingly, a body fat analyzer is able to accurately measure an accumulated amount of body fat in each body part of the user.

When the body fat is measured via the bio impedance, large electrodes are placed in direct contact with a body part of the user, and a contact resistance generated affects the measured value of the bio impedance.

SUMMARY

Methods and apparatuses consistent with exemplary embodiments provide for measuring body fat without any influence of a contact resistance between electrodes and a body part.

According to an aspect of an exemplary embodiment, there is a computer readable medium having embodied thereon a computer program for executing the above method. However, the technical goal of the inventive concept is not limited thereto, and other technical goals may be inferred from the following embodiments of the inventive concept.

Additional aspects will be set forth in part in the description which follows and, in part, will be apparent from the description, or may be learned by practice of the presented exemplary embodiments.

According to an aspect of an exemplary embodiment, a method of measuring body fat of a user, includes: measuring a first impedance by using a 4-point measuring method; measuring a second impedance by using a 2-point measuring method; determining a bio impedance by using the first impedance and the second impedance; and determining a body fat percentage by using the bio impedance and body information of the user.

The determining of the bio impedance may be performed by using a look-up table.

The determining of the bio impedance may be calculated using a central processing unit (CPU) according to values of the first impedance and the second impedance.

The measuring of the first impedance may include applying a constant current through two first electrodes among four electrodes and measuring a voltage across two second electrodes among the four electrodes.

The first two electrodes may be different than the second two electrodes.

The measuring of the second impedance may include connecting one of the first electrodes to one of the second electrodes; and measuring the second impedance by using the first electrode and the second electrode which are connected to each other.

The measuring of the second impedance may include measuring the second impedance by using two third electrodes different than the four electrodes.

According to an aspect of another exemplary embodiment, a body fat analyzer includes a plurality of electrodes configured to contact a user, the plurality of electrodes comprising two first electrodes and two second electrodes; an impedance measurer configured to measure a first impedance by using the first electrodes and the second electrodes and measure a second impedance by connecting the first electrodes with a corresponding one of the second electrodes; a bio impedance determiner configured to determine a bio impedance by using the first impedance and the second impedance; and a body fat determiner configured to determine a body fat percentage by using the bio impedance and body information of the user.

The bio impedance determiner may determine the bio impedance by inputting the first impedance and the second impedance to a look-up table.

The bio impedance determiner may include a central processing unit (CPU) configured to determine the bio impedance according to values of the first and second impedance.

The impedance measurer may be configured to apply a constant current through the first electrodes and measure the first impedance by measuring a voltage across the two second electrodes.

The first two electrodes may be different than the second two electrodes.

The impedance measurer may be configured to connect one of the first electrodes to one of the second electrodes by using a switch, and measure the second impedance by using the first electrode and the second electrode which are connected to each other.

The body fat analyzer may be a wearable device that the user wears on a wrist.

Two of the plurality of electrodes may be arranged on an inner surface of the wearable device, and two of the plurality of electrodes may be arranged on an outer surface of the wearable device.

According to an aspect of another exemplary embodiment, a body fat analyzer includes: a plurality of electrodes that contact a user when the user wears the body fat analyzer, the plurality of electrodes including four first electrodes and two second electrodes; an impedance measurer configured to measure a first impedance by using the first electrodes and the second electrodes and a second impedance by using the second electrodes; a bio impedance determiner configured to determine a bio impedance by using the first impedance and the second impedance; and a body fat determiner configured to determine a body fat percentage by using the bio impedance and body information.

According to an aspect of still another exemplary embodiment, a device for measuring body fat includes an impedance measurer configured to measure a first body impedance using a plurality of first electrodes and measure a second body impedance using a plurality of second electrodes; a bio impedance determiner configured to determine a bio impedance using the determined first body impedance and the determined second body impedance; and a body fat determiner configured to determine a body fat percentage based on the determined bio impedance and body information of the user.

The plurality of first electrodes may be a first size and the plurality of second electrodes may be a second size different from the first size.

The bio impedance determiner may be further configured to control at least one switch to connect pairs of the first electrodes to form the second electrodes.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION OF EXEMPLARY EMBODIMENTS

Hereinafter, exemplary embodiments will be described in detail with reference to the attached drawings. The present disclosure may be achieved in various forms and is not limited to the following exemplary embodiments. For convenience of description, parts not directly related to the present disclosure are omitted, and like numerals refer to like elements throughout. Expressions such as "at least one of," when preceding a list of elements, modify the entire list of elements and do not modify the individual elements of the list.

Figure 1:
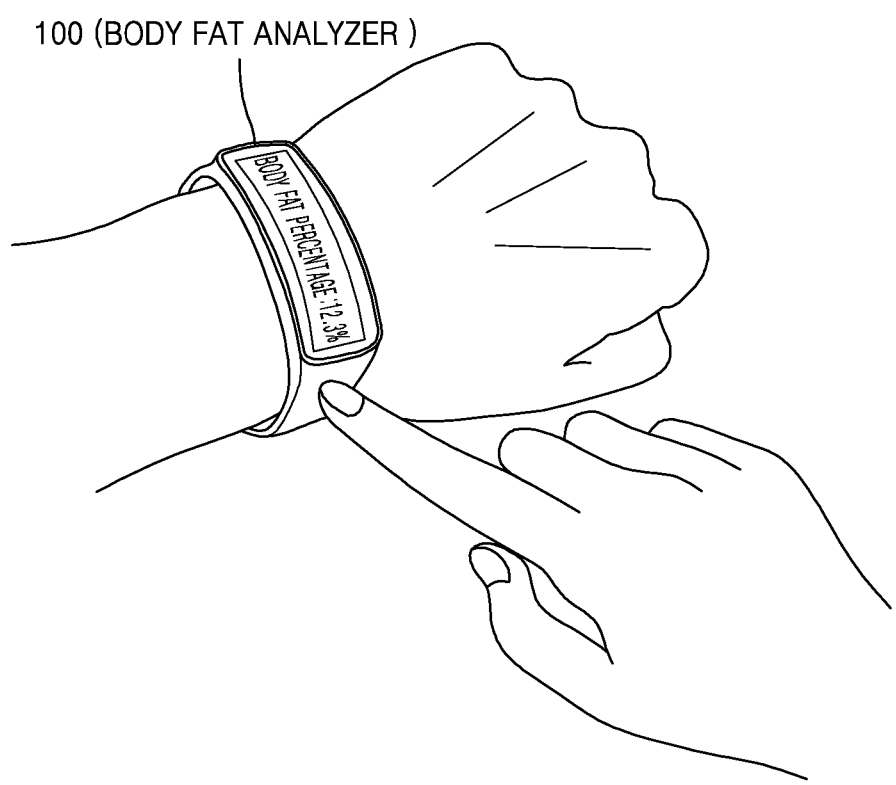
FIG. 1 illustrates a body fat analyzer according to an exemplary embodiment.

FIG. 1 illustrates a body fat analyzer 100 according to an exemplary embodiment.

A user wears the body fat analyzer 100 and touches a side thereof with a finger in order to obtain a body fat percentage. The body fat analyzer 100 applies a current to the finger via electrodes and measures a voltage between the electrodes. The body fat analyzer 100 then determines an impedance by using the measured voltage and determines a body fat percentage of the user by using the determined impedance and other body information of the user.

FIG. 1 illustrates the body fat analyzer 100 that displays the body fat percentage of the user. The exemplary user wearing the body fat analyzer 100 has a body fat percentage of about 12.3%.

Like the electrodes of the body fat analyzer 100 of FIG. 1, other small electrodes may be used to determine the body fat percentage by using a small electronic device. However, as sizes of the electrodes decrease, a contact resistance generated by contact of body parts increases. Contact resistance affects the measured value of the bio impedance. When the body fat analyzer 100 is wearable, the electrodes are smaller, and thus, it may be difficult to accurately determine the body fat percentage due to the large contact resistance. Therefore, when the body fat analyzer 100 is used, an accurate determination of the body fat percentage of the user needs an accurate measurement of the bio impedance without any influence of the contact resistance.

The body fat analyzer 100 determines the body fat percentage based on the determined bio impedance. The body fat analyzer 100 determines the body fat percentage of the user by using the bio impedance and other body information of the user. The body information of the user may include one or more of the age, height, weight, etc. of the user. The impedance measured by the body fat analyzer 100 corresponds to a voltage measured in accordance with the current applied by the body fat analyzer 100, and the bio impedance is determined using various elements, such as the contact resistance.

The body fat analyzer 100 measures impedance in two manners and then determines the bio impedance. In detail, the body fat analyzer 100 measures the impedance twice by using a different number of electrodes. For example, the body fat analyzer 100 first uses four electrodes which contact a body part of the user so as to measure a first impedance and then uses two electrodes which contact a body part of the user so as to measure a second impedance. The body fat analyzer 100 then determines the body fat percentage by using the first impedance and the second impedance.

The body fat analyzer 100 may be a wearable device, for example, a smart watch or a smart ring. The electrodes may be arranged on an inner surface of the body fat analyzer 100. The electrodes on the inner surface contact the user when the user wears the body fat analyzer 100. The electrodes may also be arranged on an outer surface of the body fat analyzer 100. The electrodes arranged on the outer surface of the body fat analyzer 100 may contact a body part of the user through a separate action of the user.

FIGS. 2A through 2D illustrate processes performed by the body fat analyzer 100 in order to determine a body fat percentage. As shown in FIGS. 2A through 2D, the body fat analyzer 100 may include a user interface.

Figure 2A:
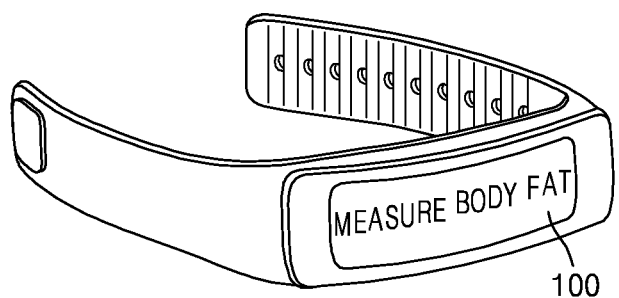
FIGS. 2A through 2D illustrate processes performed by the body fat analyzer to determine a body fat percentage.

In FIG. 2A, the body fat analyzer 100 displays the expression "measure body fat". The body fat analyzer 100 indicates that it will perform a process for measuring the body fat.

Figure 2B:
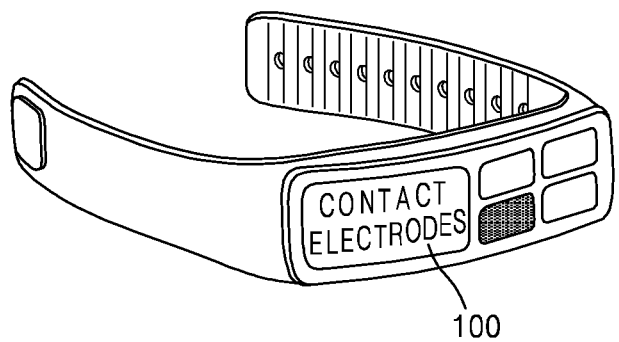

In FIG. 2B, the body fat analyzer 100 displays the expression "contact electrodes". The body fat analyzer 100 may indicate which electrodes are currently in contact with a body part of the user. In FIG. 2B, four squares are displayed on a right side of the body fat analyzer 100 to indicate the electrodes, and colors, dots, etc. in the squares indicate which of the electrodes are in contact with a body part of the user.

Figure 2C:
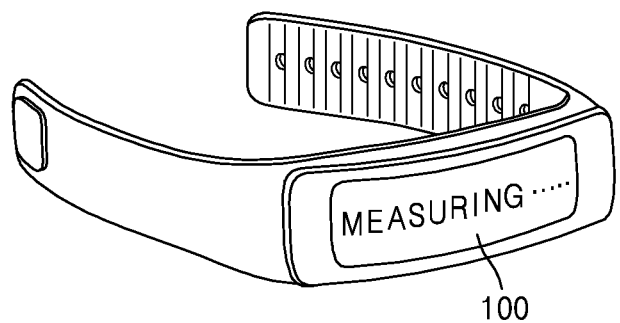

In FIG. 2C, the body fat analyzer 100 displays the expression "measuring . . . " while the bio impedance, the body fat percentage, etc. are being determined, and may inform the user of a current state.

Figure 2D:
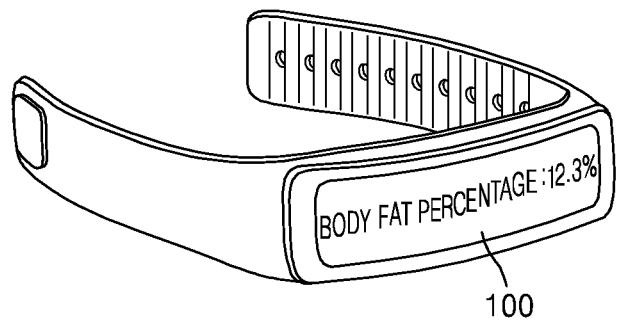

In FIG. 2D, the body fat analyzer 100 displays the expression "body fat percentage: 12.3%". The body fat analyzer 100 determines the body fat percentage of the user and displays the determined body fat percentage.

Figure 3:
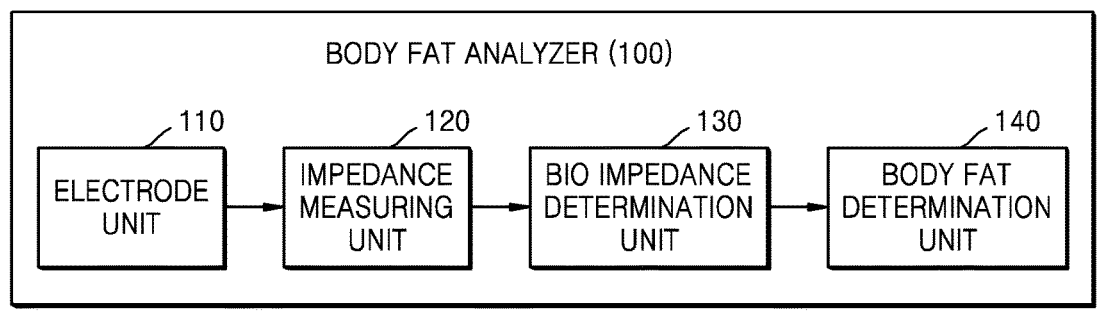
FIG. 3 is a diagram of the body fat analyzer according to an exemplary embodiment.

FIG. 3 is a diagram of the body fat analyzer 100 according to an exemplary embodiment. Referring to FIG. 3, the body fat analyzer 100 includes an electrode unit 110, an impedance measuring unit 120, a bio impedance determination unit 130, and a body fat determination unit 140. The body fat analyzer 100 may determine the bio impedance so that a determination result is independent of a contact resistance.

The electrode unit 110 includes multiple electrodes. The electrodes contact body parts of the user, and a contact resistance is generated between the electrodes and the body parts. The contact resistance is inversely proportional to sizes of the electrodes.

The body fat analyzer 100 may be a wearable device, such as a smart watch. When the body fat analyzer 100 is worn, some of the electrodes contact a body part of the user. Also, other electrodes may contact the body part of the user due to various actions of the user.

The impedance measuring unit 120 measures the impedance by using a bio impedance analyzer (BIA) method. The impedance measuring unit 120 applies a current to the body of the user through the electrodes and measures a voltage between the electrodes so as to measure the impedance. The impedance measuring unit 120 determines a ratio of the applied current to the voltage in order to measure the impedance.

The impedance measuring unit 120 first measures a first impedance with regard to the user by using a 4-point measuring method. In other words, the impedance measuring unit 120 measures the first impedance by using four electrodes. The impedance measuring unit 120 applies a constant current to the body of the user through two of four electrodes and measures the first impedance through the other two electrodes. The constant current has a constant intensity. Therefore, the impedance measuring unit 120 measures a voltage level to determine the impedance.

The impedance measuring unit 120 may change the number of electrodes used to measure the impedance from four to two and then measure a second impedance with regard to the user by using a 2-point measuring method. In other words, the impedance measuring unit 120 measures the second impedance by using two electrodes. The impedance measuring unit 120 may include a switch and may connect two electrodes by controlling the switch.

By controlling the switch, the impedance measuring unit 120 may connect a current electrode and a voltage electrode, among the four electrodes. The current electrode is an electrode to which the constant current is applied in the 4-point measuring method, and the voltage electrode is an electrode connected to a voltage meter in the 4-point measuring method. When the current and voltage electrodes are connected to each other, they operate as a single electrode having twice the area of each of the individual electrode. The impedance measuring unit 120 measures the second impedance via the current and voltage electrodes which are connected to each other using the 2-point measuring method.

According to an exemplary embodiment, the impedance measuring unit 120 may include two additional electrodes, and measure the second impedance through two additional electrodes. In other words, the body fat analyzer 100 may include six electrodes in total, perform a 4-point measurement by using four electrodes and perform a 2-point measurement by using the remaining two electrodes. The 4-point measurement and the 2-point measurement are performed with respect to the same body part of the user.

The 4-point measurement and the 2-point measurement will be described in detail with reference to FIG. 5.

The bio impedance determination unit 130 determines the bio impedance of the user by using the first impedance and the second impedance. The bio impedance is necessary to determine the body fat percentage and differs according to characteristics of a body of the user. In other words, the bio impedance differs according to the body fat percentage.

When the first impedance and the second impedance are measured, the bio impedance determination unit 130 determines the bio impedance according to the measured first impedance and the second impedance. The first impedance and the second impedance are respectively included in interaction formulas also including the bio impedance and the contact resistance as variables. The interaction formulas include a first interaction formula in which the first impedance, the bio impedance, and the contact resistance are variables. The interaction formulas also include a second interaction formula in which the second impedance, the bio impedance and the contact resistance are variables. Therefore, the bio impedance determination unit 130 may determine the bio impedance from the first and second interaction formulas, independent of the contact resistance.

The first interaction formula used in the 4-point measuring method is given by Formula 1.

$$Z_{4P} = f_1(Z_m, R_c, Z_i) = Z_m \frac{1}{1 + \frac{Z_m + 2R_c}{Z_i}} \qquad [\text{Formula 1}]$$

where $Z_{4P}$ is the first impedance measured using a voltage meter, $Z_m$ is a desired bio impedance, $R_C$ is a contact resistance, Zi is impedance of an analog front end (AFE), and the AFE is an analog circuit. Referring to Formula 1, if Zi is infinite, $Z_{4P}$ and $Z_m$ are identical. However, Zi is actually finite, and thus, as the contact resistance increases, $Z_{4P}$ becomes smaller than $Z_m$.

Also, the second interaction formula used in the 2-point measuring method is given by Formula 2.

$$Z_{2P} = f_2(Z_m, R_c, Z_i) = \frac{1}{\frac{1}{Z_m + R_c} + \frac{1}{Z_i}} \qquad [\text{Formula 2}]$$

where $Z_{2P}$ is the second impedance measured by using the voltage meter.

Referring to Formula 1 and Formula 2, $Z_{4P}$ and $Z_{2P}$ are measured values, and Zi is a value determined according to properties of the AFE. Therefore, Formula 1 and Formula 2 may be simultaneously solved to determine $Z_m$ and Rc. Although a value of $R_C$ is not found or determined, $Z_m$ may be determined.

According to an exemplary embodiment, the bio impedance determination unit 130 determines the bio impedance with regard to the first impedance and the second impedance by using a look-up table stored in memory. The first impedance and the second impedance are input to the look-up table, the bio impedance is output from the look-up table, and the values of the bio impedance determined according to the first impedance and the second impedance are stored in the look-up table.

Also instead of using a look-up table, the bio impedance determination unit 130 may include CPU which calculates the bio impedance according to values of the first impedance and the second impedance. The CPU may determine the bio impedance by using the first interaction formula, the second interaction formula, the first impedance, and the second impedance.

The body fat determination unit 140 determines the body fat percentage of the user by using the bio impedance and the body information of the user. The body information of the user is received from the user. The body information of the user may include information such as age, height, weight, or the like of the user.

Figure 4:
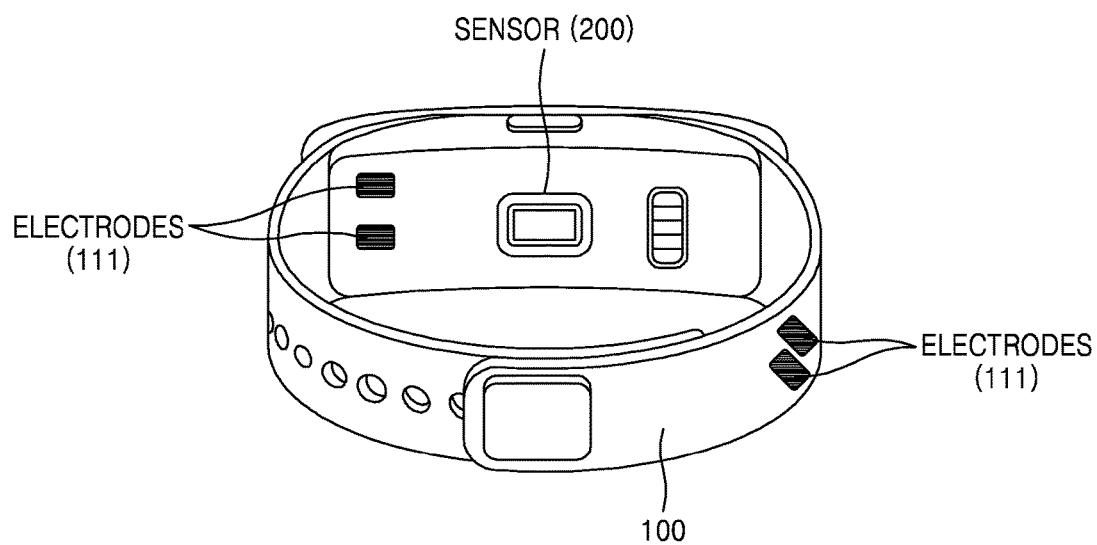
FIG. 4 illustrates the body fat analyzer according to an exemplary embodiment.

FIG. 4 illustrates the body fat analyzer 100 according to an exemplary embodiment. Referring to FIG. 4, the body fat analyzer 100 includes electrodes 111 and a sensor 200. The body fat analyzer 100 of FIG. 4 includes four electrodes 111 identical in size and composition, but the number, size, and composition of electrodes are not limited thereto.

FIG. 4 illustrates an exemplary embodiment where the body fat analyzer 100 is a smart watch.

The electrodes 111 may contact a body part of the user. Two of the electrodes 111 are arranged on an inner surface of the body fat analyzer 100, and the other two of the electrodes 111 are arranged on an outer surface of the body fat analyzer 100. For example, when the user wears the body fat analyzer 100 on the left wrist, the two of the electrodes 111, which are arranged on the inner surface of the body fat analyzer 100, naturally contact the body part of the user. Also, the other electrodes 111 may come in contact with the right hand of the user. In other words, the user may touch the electrodes 111 which are arranged on the outer surface of the body fat analyzer 100 with the right hand.

The sensor 200 detects whether the user wears the body fat analyzer 100. The sensor 200 may be a proximity sensor, a temperature sensor, or the like. If the sensor 200 is a proximity sensor, a distance between the sensor 200 and the user is measured. Therefore, when the sensor 200 and the user are within a certain distance from each other, the body fat analyzer 100 may determine that the user is wearing the body fat analyzer 100. If the sensor 200 is a temperature sensor, the sensor 200 may detect a temperature, and when a certain temperature is detected, the body fat analyzer 100 may determine that the user is wearing the body fat analyzer 100. When the body fat analyzer 100 determines that the user is wearing the body fat analyzer 100, the body fat analyzer 100 may perform a process for determining the body fat percentage.

Figure 5:
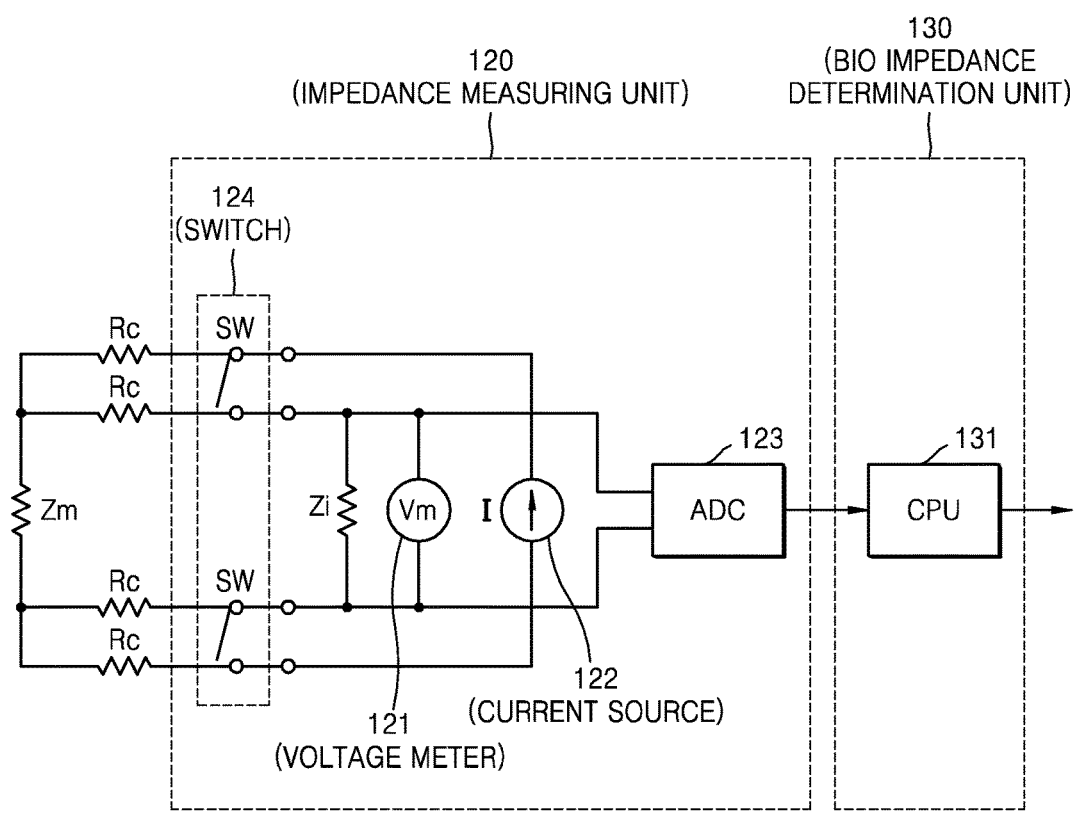
FIG. 5 is a circuit diagram of the body fat analyzer according to an exemplary embodiment.

FIG. 5 is a circuit diagram of the body fat analyzer 100 according to an exemplary embodiment. Referring to FIG. 5, the body fat analyzer 100 includes a switch 124 for interconnecting the electrodes according to the 4-point measuring method and the 2-point measuring method.

Regarding FIG. 5, $Z_m$ is a bio impedance and indicates a body part impedance, $R_C$ is a contact resistance generated by the electrodes 111, SW indicates the switches 124, Zi is an impedance of AFE, Vm is a voltage meter 121, I is a current source 122, ADC is an analog to digital converter 123, and CPU is a central processing unit 131.

The impedance measuring unit 120 includes the switches 124, the voltage meter 121, the current source 122, and the ADC 123. The impedance measuring unit 120 converts a measured voltage from an analog value to a digital value and outputs the converted value to the CPU 131. The switches 124 may electrically connect pairs of the four electrodes 111 to form two electrodes 111. Specifically, the switches 124 may respectively connect a terminal to which a current is applied and a terminal where a voltage is measured. Therefore, when the switches 124 are closed, the four electrodes 111 are reconfigured to function as two electrodes 111. If each of the four electrodes 111 is identical in size, each of the reconfigured two electrodes 111 is twice the size of one of the four electrodes.

The current source 122 applies a current to the body part of the user through the electrodes 111. The current source 122 may apply a current having a constant intensity to the body part of the user.

The voltage meter 121 measures a voltage between the electrodes 111. The voltage meter 121 outputs the measured voltage to the ADC 123.

The ADC 123 converts an input voltage from an analog form to a digital form. Because an intensity of the current is fixed, an intensity of the measured voltage may be proportional to the bio impedance.

The bio impedance determination unit 130 includes the CPU 131. The CPU 131 may determine the bio impedance according to an input digital voltage. The CPU 131 calculates the bio impedance according to the first interaction formula, the second interaction formula, and the two voltages which are input. The two voltages are a voltage measured by using the four electrodes 111 and a voltage measured by using the two electrodes 111.

Figure 6:
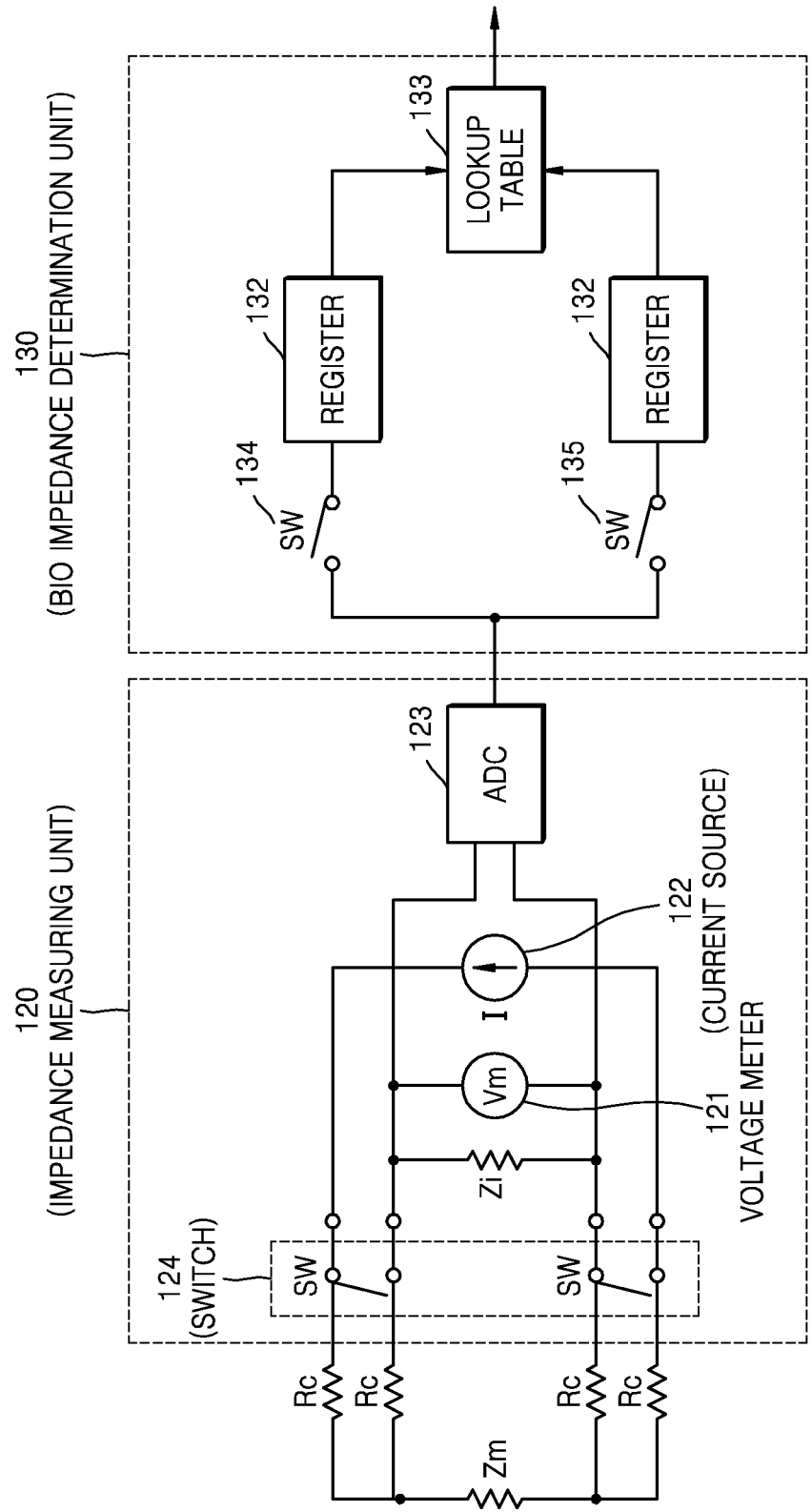
FIG. 6 is a circuit diagram of the body fat analyzer according to an exemplary embodiment.

FIG. 6 is a circuit diagram of the body fat analyzer according to an exemplary embodiment. Referring to FIG. 6, the bio impedance determination unit 130 may determine the bio impedance by using a look-up table 133 stored in memory.

The bio impedance acquiring unit 130 includes two switches 134 and 135, registers 132, and the look-up table 133.

Whether the switches are connected is determined according to the measuring method being used. For example, when the 4-point measuring method is used, an upper switch 134 may be closed and a lower switch 135 may be open. When the 2-point measuring method is used, the upper switch 134 may be open and the lower switch 135 may be closed. The registers 132 may store voltages. For example, when the 4-point measuring method is used, voltages may be stored in an upper register 132, and when the 2-point measuring method is used, voltages may be stored in a lower register 132.

The voltages stored in the registers 132 are cross-referenced with the look-up table 133, and a bio impedance value corresponding to the voltages in the look-up table is determined. When two voltages are stored in the look-up table 133, the look-up table 133 determines values corresponding to the two values. For example, the look-up table 133 may be a 2-dimensional table storing voltages. A horizontal axis indicates an impedance measured using the 4-point measuring method, and a vertical axis indicates impedance measured using the 2-point measuring method. Therefore, when values of the horizontal axis and the vertical axis are determined, a bio impedance corresponding to the values on the horizontal axis and the vertical axis may be determined from the look-up table.

The CPU extracts the bio impedance from the look-up table 133 and outputs the determined value to the body fat determination unit 140.

Figure 7:
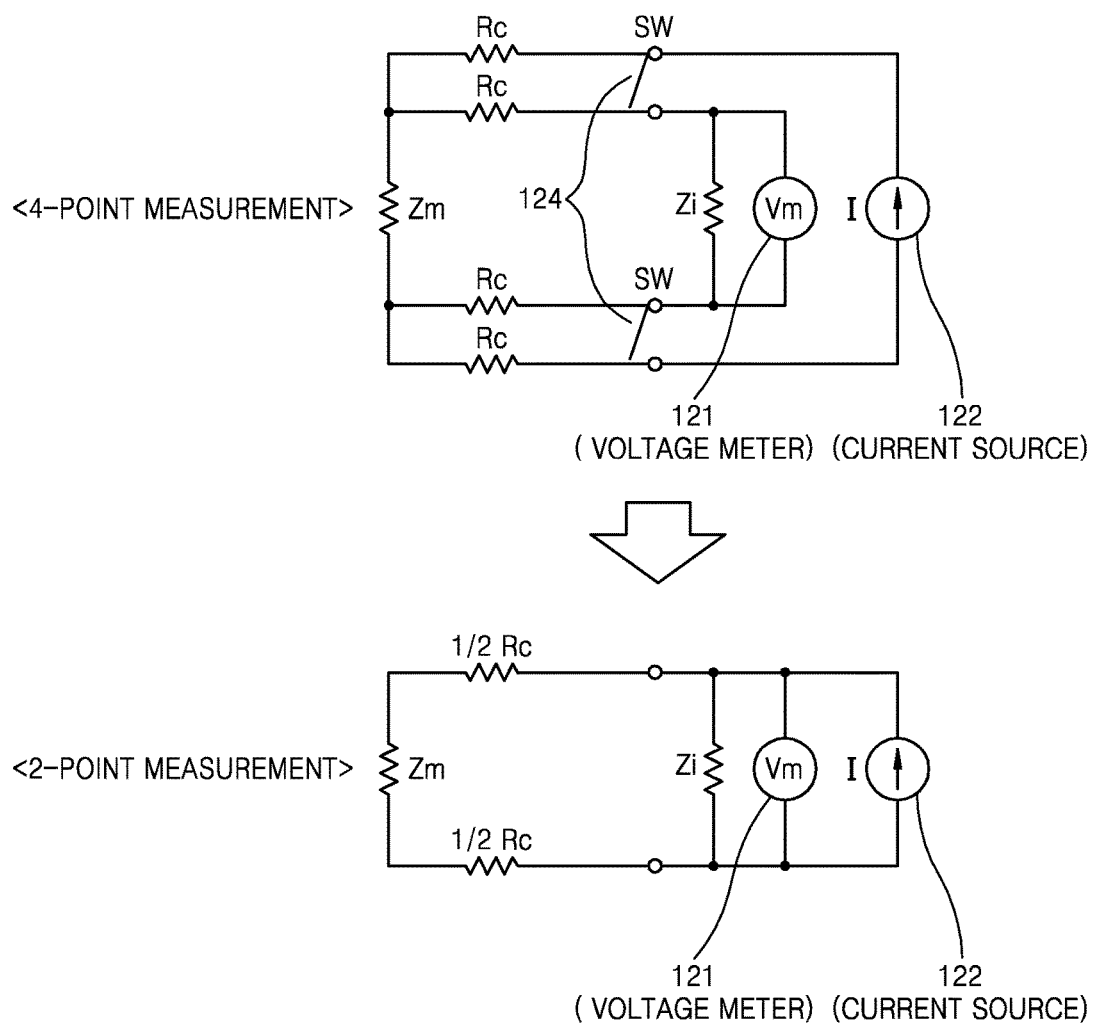
FIG. 7 is a circuit diagram of a process in which a 4-point measuring method is converted into a 2-point measuring method according to an exemplary embodiment.

FIG. 7 is a circuit diagram of a process of changing a 4-point measuring method to a 2-point measuring method. Referring to FIG. 7, the electrodes 111 are first disconnected and then the switches 124 may be closed, connecting the electrodes 111 to each other, and thus, the number of electrodes 111 changes from four to two.

When the body fat analyzer 100 measures the impedance using the 4-point measuring method, the current source 122 and the voltage meter 121 are respectively connected to different electrodes 111.

When the body fat analyzer 100 measures the impedance using the 2-point measuring method, the current source 122 and the voltage meter 121 are connected to the same electrode 111.

When the electrodes 111 are electrically connected to each other via the switch 124, a contact resistance between the electrodes 111 and the body parts decreases to half the contact resistance, as shown in the circuit diagram for explaining the 2-point measurement. Therefore, a contact resistance Rc of the 4-point measurement becomes ½ Rc in the 2-point measurement.

Figure 8:
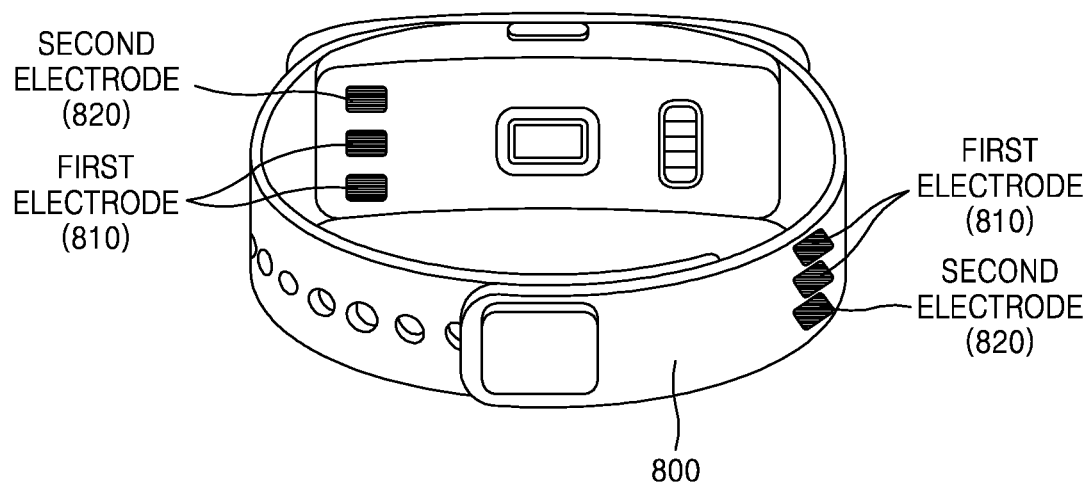
FIG. 8 illustrates the body fat analyzer according to another exemplary embodiment.

FIG. 8 illustrates the body fat analyzer 800 according to another exemplary embodiment. Referring to FIG. 8, the body fat analyzer 800 further includes second electrodes 820.

In the body fat analyzer 800 of FIG. 4, the number of electrodes 111 changes from four to two, and then the impedance is measured. In the exemplary body fat analyzer 100 of FIG. 8, second electrodes 820 are further included in addition to first electrodes 810. Therefore, the body fat analyzer 800 of FIG. 8 does not require the switch 124 and a process for changing the number of electrodes. Accordingly, the body fat analyzer of FIG. 8 may quickly measure the first impedance and the second impedance.

The body fat analyzer 800 includes two pairs of first electrodes 810 and one pair of the second electrodes 820. Two first electrodes 810 are arranged on the inner surface of the body fat analyzer 800, and other two first electrodes 810 are arranged on the outer surface of the body fat analyzer 800. One second electrode 820 is arranged on the inner surface of the body fat analyzer 800, and the other second electrode 820 is arranged on the outer surface of the body fat analyzer 800. Therefore, three electrodes are respectively arranged on the inner surface of the body fat analyzer 800 and three electrodes are respectively arranged on the outer surface of the body fat analyzer 800. For example, the electrodes 810 and 820 may be arranged on the inner surface of the body fat analyzer 800 in parallel or may be arranged adjacent to each other. Also, the electrodes 810 and 820 may be arranged on the outer surface of the body fat analyzer 800 in parallel or may be arranged adjacent to each other.

The first electrodes 810 are used to measure the first impedance using the 4-point measuring method, and the second electrodes 820 are used to measure the second impedance using the 2-point measuring method.

When the 4-point measuring method is performed, an interface formula which is the same as Formula 1 is used. When the 2-point measuring method is performed, the following Formula 3 is used.

$$Z_{2P} = f_2(Z_m, R_c, Z_i) = \frac{1}{\frac{1}{Z_m + 2R_c} + \frac{1}{Z_i}}$$ [Formula 3]

Figure 9:
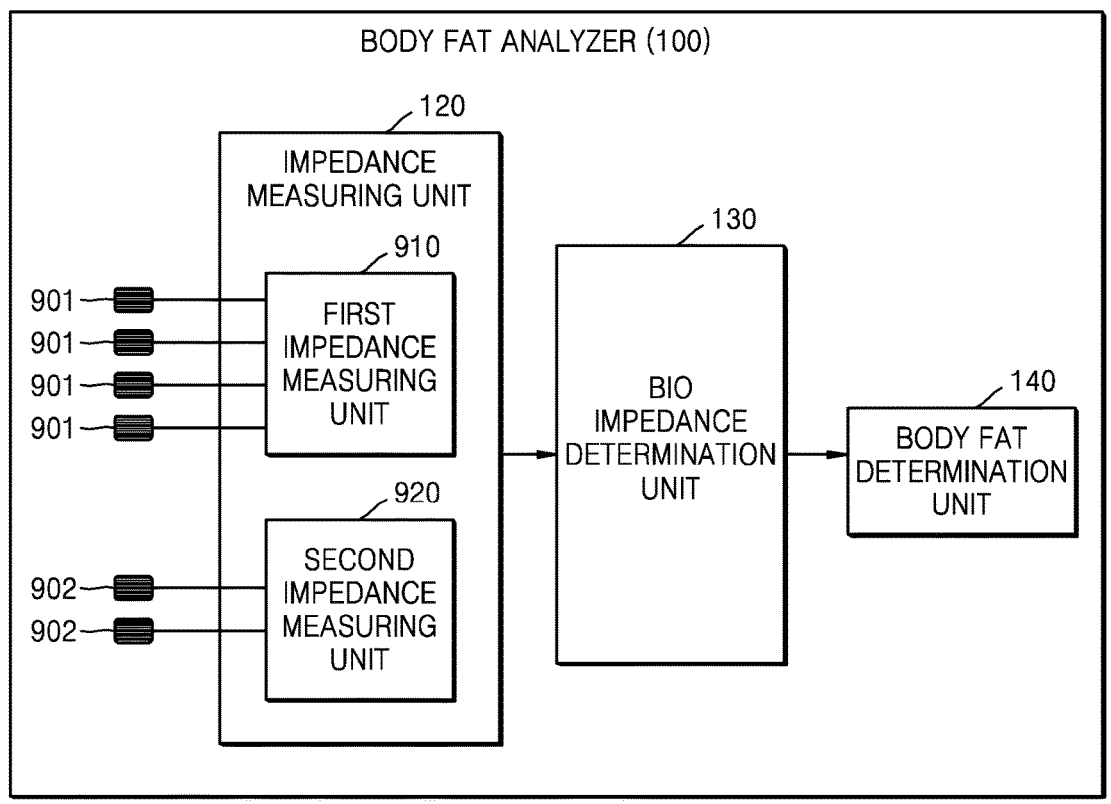
FIG. 9 is a diagram of the body fat analyzer according to another exemplary embodiment.

FIG. 9 illustrates a diagram of the body fat analyzer of FIG. 8. Referring to FIG. 9, the impedance measuring unit 120 includes a first impedance measuring unit 910 and a second impedance measuring unit 920.

The first impedance measuring unit 910 is connected to four electrodes 901, and the second impedance measuring unit 920 is connected to two electrodes 902. The electrodes 901 correspond to the first electrodes 810 of FIG. 8, and the electrodes 902 correspond to the second electrodes 820 of FIG. 8.

The first impedance measuring unit 910 measures a first impedance by using the electrodes 901 and measures a second impedance by using the electrodes 902. The impedance measuring unit then outputs the measured first and second impedance to the bio impedance acquiring unit 130.

Figure 10:
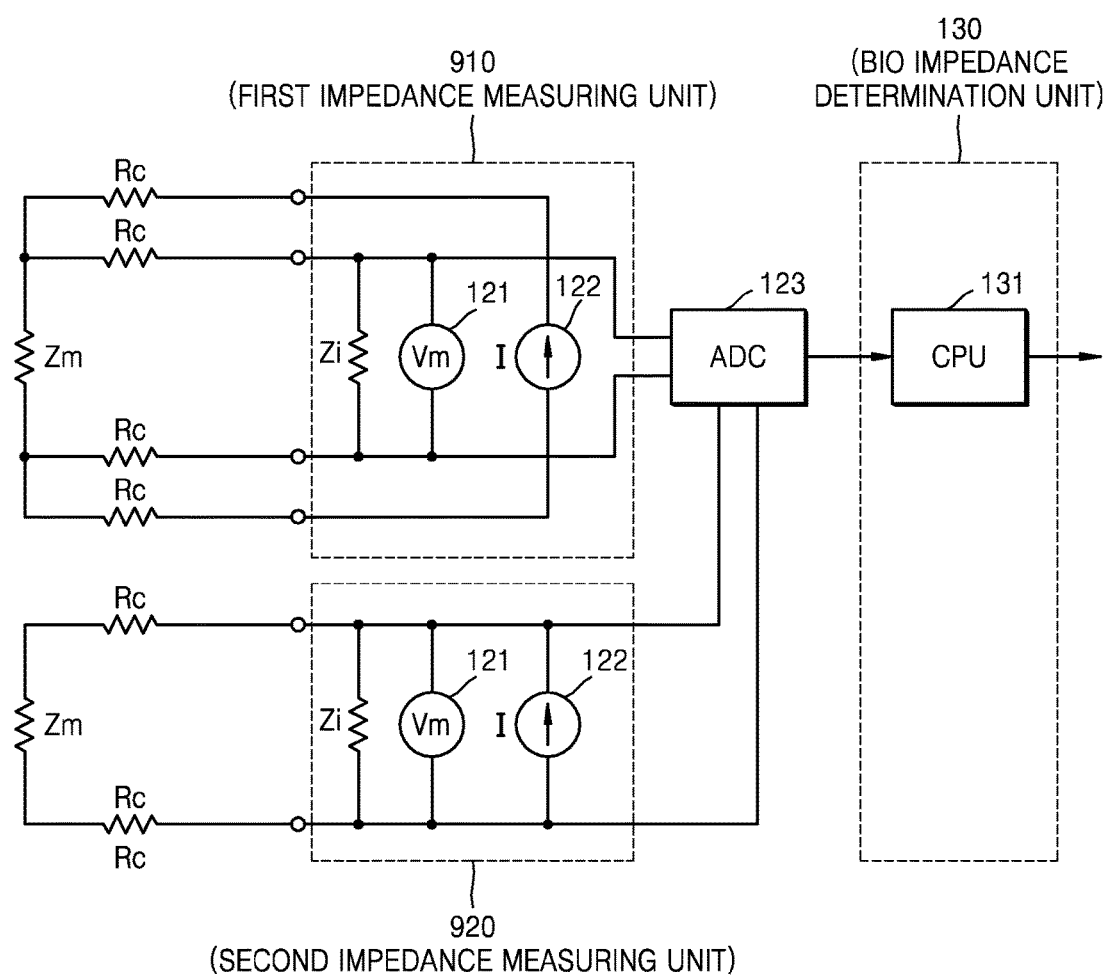
FIG. 10 is a circuit diagram of the body fat analyzer according to another exemplary embodiment.

FIG. 10 is a circuit diagram of the body fat analyzer 800 according to another exemplary embodiment. Referring to FIG. 10, the first impedance measuring unit 910 and the second impedance measuring unit 920 may be implemented as separate circuits.

The first impedance measuring unit 910 and the second impedance measuring unit 920 each include a voltage meter 121 and a current source 122. Therefore, the first impedance measuring unit 910 and the second impedance measuring unit 920 may independently measure a respective impedance. The first impedance measuring unit 910 and the second impedance measuring unit 920 may simultaneously or sequentially measure a first impedance and a second impedance.

The first impedance measuring unit 910 and the second impedance measuring unit 920 respectively output the first measured impedance and the second measured impedance, which are indicated by voltage values, to the ADC 123. The ADC 123 converts the received voltage values into digital signals and outputs the converted digital signals to the CPU 131. The CPU 131 may determine the bio impedance by using the two output voltages converted to the digital signals.

Figure 11:
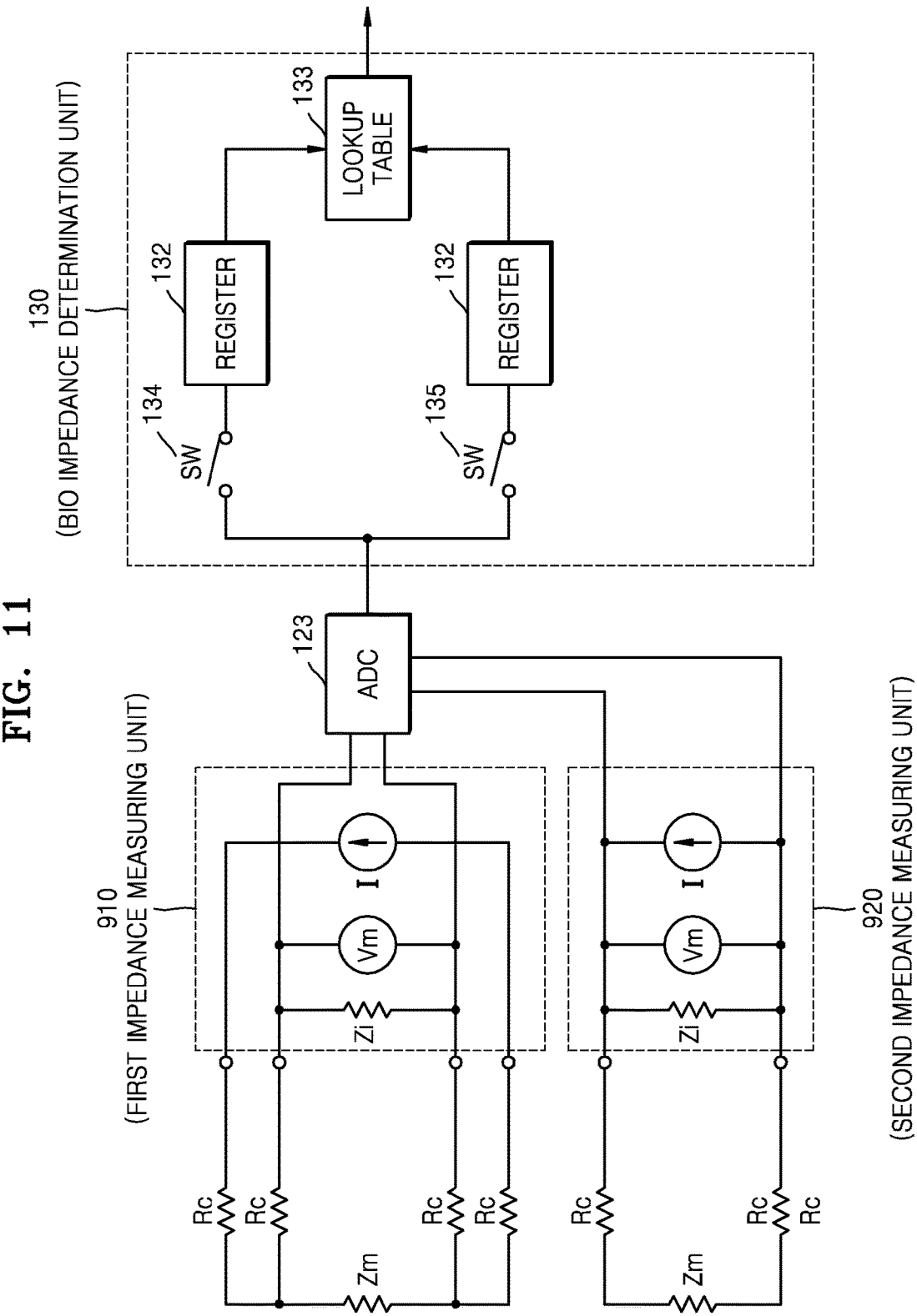
FIG. 11 is a circuit diagram of the body fat analyzer according to another exemplary embodiment.

FIG. 11 is a circuit diagram of the body fat analyzer 800 according to another exemplary embodiment. According to the exemplary embodiment of FIG. 10, the CPU 131 determines the bio impedance based on the measured voltages. According to the exemplary embodiment of FIG. 11, the bio impedance is determined via the look-up table 133, based on the impedance values stored in the registers 132. The bio impedance determination units 130 of FIG. 6 and FIG. 11 have the same structure, but the electrodes 111 and the impedance measuring units 120 thereof have different structures. Therefore, the descriptions with regard to the bio impedance acquiring unit 130 of FIG. 6 are the same as those with regard to the bio impedance acquiring unit 130 of FIG. 11.

Figure 12:
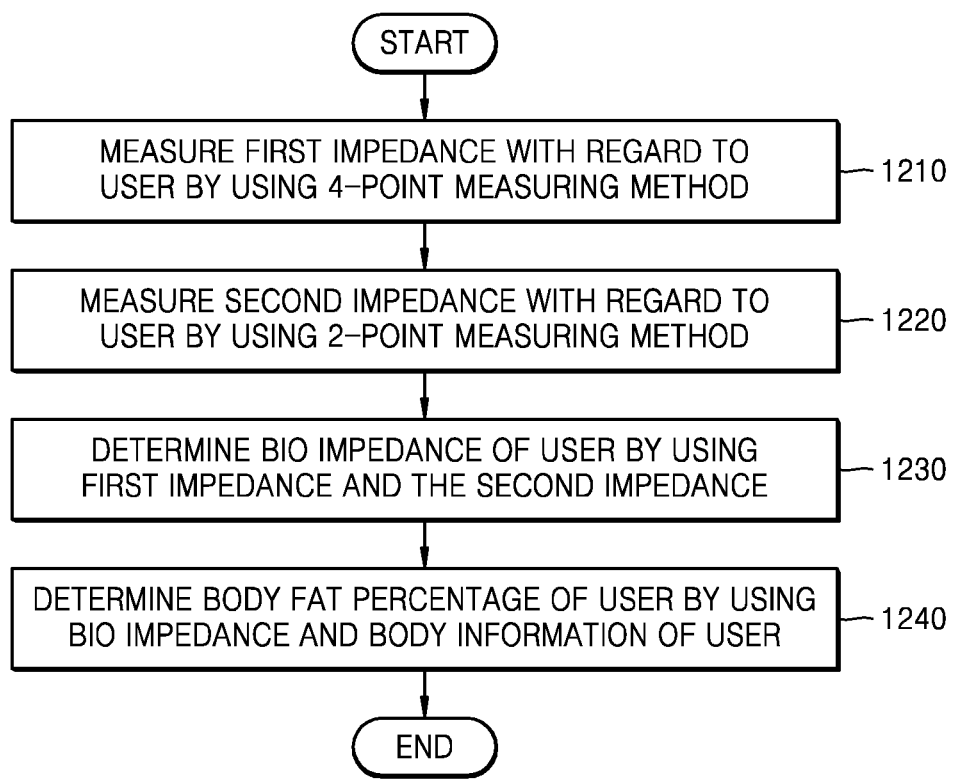
FIG. 12 is a flowchart illustrating a method of measuring body fat, according to an exemplary embodiment.

FIG. 12 is a flowchart illustrating a method of measuring body fat, according to an exemplary embodiment. Referring to FIG. 12, the body fat analyzer 100 may determine a body fat percentage by using two measuring methods.

In operation 1210, the body fat analyzer measures a first impedance using a 4-point measuring method. The body fat analyzer measures the first impedance by using four electrodes. Two of the four electrodes are used to apply a current to the body of the user and the other two electrodes are used to measure a voltage.

In operation 1220, the body fat analyzer measures a second impedance using the 2-point measuring method. The body fat analyzer measures the second impedance by using two electrodes. The electrodes are used to simultaneously apply a current and measure a voltage. The body fat analyzer may electrically change the four electrodes into two electrodes. Also, the body fat analyzer may further include two electrodes in addition to the four electrodes.

In operation 1230, the body fat analyzer determines the bio impedance of the user by using the first impedance and the second impedance. The body fat analyzer may determine the bio impedance without any influence due to a contact resistance. The body fat analyzer determines the bio impedance without any influence of the contact resistance by using a first interaction formula with regard to the first impedance and a second interaction formula with regard to the second impedance. Therefore, although sizes of the electrodes are small, the body fat analyzer may accurately measure the bio impedance.

In operation 1240, the body fat analyzer determines a body fat percentage of the user by using the bio impedance and body information of the user. The body fat analyzer receives one or more of the age, height, weight, etc. from the user and determines the body fat percentage based on the received body information and the bio impedance. The determined body fat percentage is displayed on a display unit as shown in FIG. 2.

Figure 13:
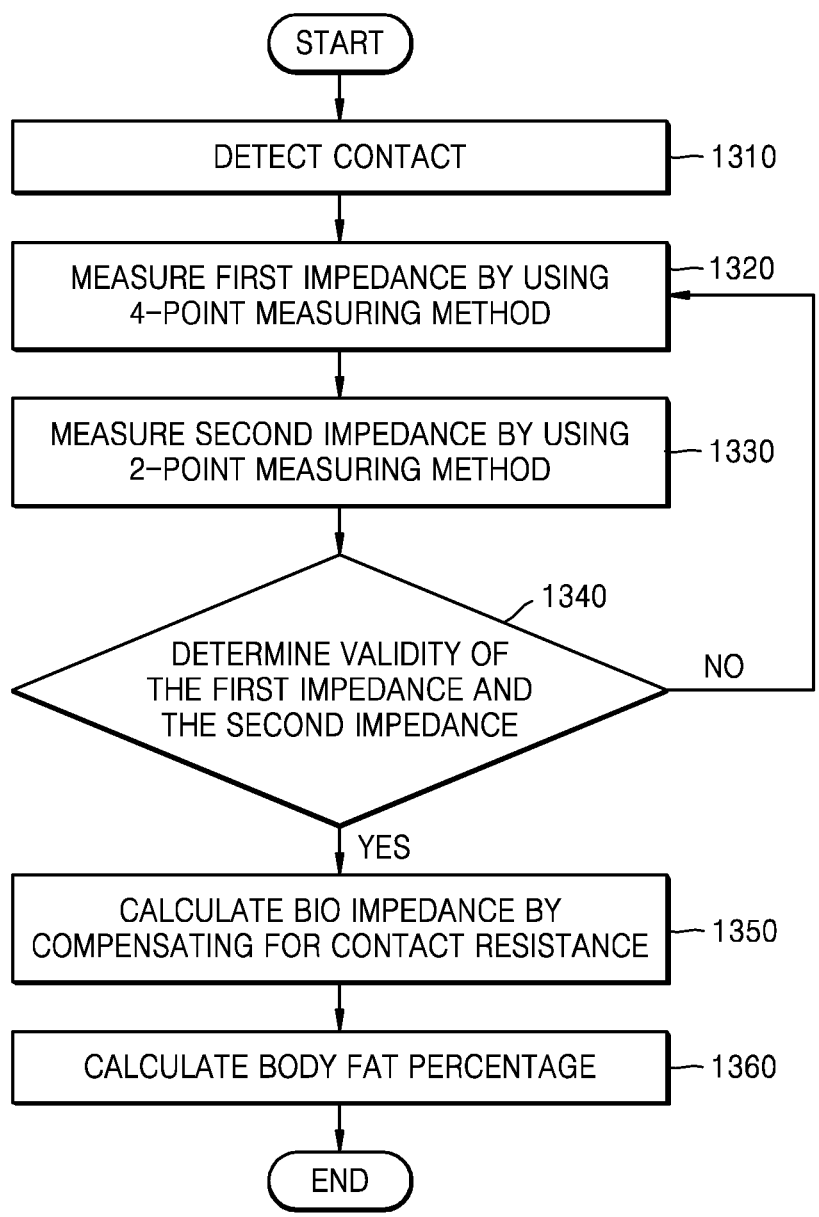
FIG. 13 is a flowchart illustrating a method of measuring body fat, according to an exemplary embodiment.

FIG. 13 is a flowchart illustrating a method of measuring body fat, according to an exemplary embodiment. Referring to FIG. 13, the body fat analyzer may determine a body fat percentage using two methods.

In operation 1310, the body fat analyzer detects a contact state for each of the electrodes 111. The body fat analyzer determines whether each of the electrodes makes contact with the body.

In operation 1320, the body fat analyzer measures a first impedance using the 4-point measuring method.

In operation 1330, the body fat analyzer measures a second impedance using the 2-point measuring method.

In operation 1340, the body fat analyzer determines the validity of the first impedance and the second impedance. For example, the body fat analyzer may determine the validity of the first impedance and the second impedance according to a contact state of the electrodes 111. If the impedance is measured without the electrodes 111 contacting the body of the user, the measurement value is considered to be invalid. Therefore, the body fat analyzer the validity of the measurement results may be determined by checking the state of the various electrodes when the impedance is measured.

In another example, the body fat analyzer may determine the validity of the impedance according to a value of the measured impedance. The body fat analyzer may set an impedance range corresponding to a human body and may determine the validity of the measured impedance by checking whether the measured impedance is in the above range.

If the first impedance and the second impedance are valid, operation 1350 is performed, and if the first impedance and the second impedance are invalid, operation 1320 is again performed.

In operation 1350, the body fat analyzer determines the bio impedance of the user by using the first impedance and the second impedance.

In operation 1360, the body fat analyzer determines the body fat percentage of the user by using the bio impedance and the body information of the user. The body fat analyzer receives one or more of the age, height, weight, etc. from the user and determines the body fat percentage based on the received body information and the bio impedance.

As described above, according to one or more exemplary embodiments, a body fat analyzer may determine a body fat percentage without any influence of a contact resistance. Accordingly, the body fat analyzer may determine the body fat percentage by using a small-sized electrode.

The body fat analyzer described herein may comprise a processor, a memory for storing and executing program data, a permanent storage unit, such as a disk drive, a communications port communicating with external devices, and one or more user interface devices, such as a touch panel, keys, buttons, etc. Software modules or algorithms may be stored as program instructions or computer readable codes executable on a processor on a computer-readable medium. Examples of the computer readable recording medium include read only memory (ROM), magnetic storage media (e.g., floppy disks, hard disks, etc.), and optical recording media (e.g., CD-ROMs, or DVDs). The computer readable recording medium can also be distributed over network coupled computer systems so that the computer readable code is stored and executed in a distributive manner. This media can be read by the computer, stored in the memory, and executed by the processor.

Exemplary embodiments may be described in terms of functional block components and various processing steps. Such functional blocks may be realized by any number of hardware and/or software components configured to perform the specified functions. For example, the present invention may employ various integrated circuit (IC) components, e.g., memory elements, processing elements, logic elements, look-up tables, and the like, which may carry out a variety of functions under the control of one or more microprocessors or other control devices. Similarly, where the elements of the present invention are implemented using software programming or software elements, the invention may be implemented with any programming or scripting language, such as C, C++, Java, assembler language, or the like, with the various algorithms being implemented with any combination of data structures, objects, processes, routines or other programming elements. Functional aspects may be implemented in algorithms that are executed on one or more processors. Furthermore, exemplary embodiments could employ any number of conventional techniques for electronics configuration, signal processing and/or control, data processing and the like. The words "mechanism", "element", "means", and "configuration" are used broadly and are not limited to mechanical or physical embodiments, but can include software routines in conjunction with processors, etc.

The particular implementations shown and described herein are illustrative examples and are not intended to otherwise limit the scope of the disclosure in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing exemplary embodiments (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The exemplary embodiments are not limited to the described order of the steps. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to one of ordinary skill in the art without departing from the spirit and scope of the present disclosure.

What is claimed is:

1. A method of measuring body fat of a user, the method comprising:

measuring a first impedance of the user by using a 4-point measuring method, wherein the measuring of the first impedance comprises applying, by a current source, a constant current through two first electrodes among four electrodes while measuring, by a voltage meter, a voltage across two second electrodes among the four electrodes;

measuring a second impedance of the user by using a 2-point measuring method, wherein the measuring of the second impedance comprises respectively connecting the two first electrodes to the two second electrodes via measuring method changing switches, to form two electrodes and measuring the second impedance by using the two formed electrodes;

determining a bio-impedance of the user based on the first impedance and the second impedance, and by closing a first switch and opening a second switch to transmit a value of the first impedance to a look-up table via the first switch while the 4-point, measuring method is performed, and opening the first switch and closing the second switch to transmit a value of the second impedance to the look-up table via the second switch while the 2-point measuring method is performed; and determining a body fat percentage of the user by using the bio-impedance and body information of the user, wherein the first switch is disposed between the look-up table and an impedance measuring circuit that includes the current source, the voltage meter, and the measuring method changing switches, and wherein the second switch is disposed between the look-up table and the impedance measuring circuit, and connected in parallel with the first switch.

2. The method of claim 1, wherein the determining of the bio-impedance is calculated using a central processing unit (CPU) according to the values of the first impedance and the second impedance.

3. The method of claim 1, wherein the determining the bio-impedance of the user based on the first impedance and the second impedance comprises combining a first formula and a second formula, wherein the first formula is expressed as:

$$Z_{4P} = Z_m \frac{1}{1 + \frac{Z_m + 2R_c}{Z_i}}$$

wherein the second formula is expressed as:

$$Z_{2P} = \frac{1}{\frac{1}{Z_m + R_c} + \frac{1}{Z_i}}$$

wherein $Z_{4P}$ denotes the first impedance, $Z_{2P}$ denotes the second impedance, $Z_m$ denotes the bio-impedance of the user, $R_C$ denotes a contact resistance between the user and the four electrodes, $Z_i$ denotes a predetermined impedance of an analog front end of a body impedance measuring circuit that performs the 4-point measuring method and the 2-point measuring method.

4. A non-transitory computer readable medium having embodied thereon a computer program, which when executed by a computer, performs the method of claim 1.

5. A body fat analyzer comprising:

a plurality of electrodes configured to contact a user, the plurality of electrodes comprising two first electrodes and two second electrodes;

an impedance measurer configured to measure a first impedance by applying a constant current through the two first electrodes while measuring a voltage across the two second electrodes and measure a second impedance by respectively connecting the two first electrodes to the two second electrodes to form two electrodes and measuring the second impedance by using the two formed electrodes;

a bio-impedance determiner configured to determine a bio-impedance based on the first impedance and the second impedance, and by closing a first switch and opening a second switch to transmit a value of the first impedance to a look-up table via the first switch while the first impedance is measured, and opening the first switch and closing the second switch to transmit a value of the second impedance to the look-up table via the second switch while the second impedance is measured; and a body fat determiner configured to determine a body fat percentage by using the bioimpedance and body information of the user, wherein the first switch is disposed between the impedance measurer and the look-up table, and wherein the second switch is disposed between the impedance measurer and the look-up table and connected in parallel with the first switch.

6. The body fat analyzer of claim 5, wherein the bio-impedance determiner comprises a central processing unit (CPU) configured to determine the bio-impedance according to the values of the first impedance and the second impedance.

7. The body fat analyzer of claim 5, wherein the two first electrodes are different than the two second electrodes.

8. The body fat analyzer of claim 5, wherein the body fat analyzer is a wearable device that the user wears on a wrist.

9. The body fat analyzer of claim 8, wherein two of the plurality of electrodes are arranged on an inner surface of the wearable device, and two of the plurality of electrodes are arranged on an outer surface of the wearable device.

10. A body fat analyzer comprising:

a plurality of electrodes that come in contact with a user when the user wears the body fat analyzer, the plurality of electrodes comprising four first electrodes and two second electrodes;

an impedance measurer configured to measure a first impedance by applying a constant current through two electrodes among the four first electrodes while measuring a voltage across the other two electrodes among the four first electrodes and measure a second impedance by using the two second electrodes;

a bio-impedance determiner configured to determine a bio-impedance based on the first impedance and the second impedance, and by closing a first switch and opening a second switch to transmit a value of the first impedance to a look-up table via the first switch while the first impedance is measured, and opening the switch and closing the second switch to transmit a value of the second impedance to the look-op table via the second switch while the second impedance is measured; and a body fat determiner configured to determine a body fat percentage by using the bioimpedance and body information, wherein the first switch is disposed between the impedance measurer and the look-up table, and wherein the second switch is disposed between the impedance measurer and the look-up table and connected in parallel with the first switch.

11. A device for measuring body fat, the device comprising:

an impedance measurer configured to measure a first body impedance by applying a constant current through two electrodes among a plurality of first electrodes while measuring a voltage across another two electrodes among the plurality of first electrodes and measure a second body impedance using a plurality of second electrodes;

a bio-impedance determiner configured to determine a bio-impedance of a user based on the first body impedance and the second body impedance, and by closing a first switch and opening a second switch to transmit a value of the first impedance to a look-up table via the first switch while the first impedance is measured, and opening the first switch and closing the second switch to transmit a value of the second impedance to the look-up table via the second switch while the second impedance is measured; and a body fat determiner configured to determine a body fat percentage of the user based on the determined bio-impedance and body information of the user;

wherein the first switch is disposed between the impedance measurer and the look-up table, and wherein the second switch is disposed between the impedance measurer and the look-up table and connected in parallel with the first switch.

12. The device of claim 11, wherein the plurality of first electrodes are a first size and the plurality of second electrodes are a second size different from the first size.

13. A method of measuring body fat of a user comprising:

measuring a first impedance of the user by applying a constant current from a current source to two electrodes among a first number of first electrodes while measuring, by a voltage meter, a voltage across another two electrodes among the first number of first electrodes;

measuring a second impedance of the user using a second number of electrodes;

determining a bio-impedance of the user based on the first and second impedances, and by closing a first switch and opening a second switch to transmit a value of the first impedance to a look-up table via the first switch while the first impedance is measured, and opening the first switch and closing the second switch to transmit a value of the second impedance to the look-up table via the second switch while the second impedance is measured; and determining the body fat of the user using the bio-impedance and body information of the user, wherein the first switch is disposed between the look-up table and an impedance measuring circuit that includes the current source and the voltage meter, and wherein the second switch is disposed between the look-up table and the impedance measuring circuit, and connected in parallel with the first switch.

14. The method of claim 13, wherein the first number of electrodes is four and the second number of electrodes is two.

15. The method of claim 14, wherein the four electrodes used in measuring the first impedance are different from the two electrodes used in measuring the second impedance.

16. The method of claim 14, wherein the two electrodes used in measuring the second impedance are also used in measuring the first impedance.

17. The method of claim 14, wherein the four electrodes used in measuring the first impedance are identical in size.

18. The method of claim 14, wherein each of the two electrodes used in measuring the second impedance is greater in size than each of the four electrodes used in measuring the first impedance.

19. The method of claim 13, wherein a same level of current is applied to the user while measuring the first and second impedances.

* * * * *